United States Patent [19]

Watson

[11] 3,933,599

[45] Jan. 20, 1976

[54] NITROSYL CHLORIDE AS A POLYMERIZATION INHIBITOR FOR VINYL AROMATIC COMPOUNDS

[75] Inventor: James M. Watson, Big Spring, Tex.

[73] Assignee: Cosden Technology, Inc., Big Spring, Tex.

[22] Filed: Dec. 9, 1974

[21] Appl. No.: 530,988

[52] U.S. Cl. ............... 203/9; 260/669 A; 423/386
[51] Int. Cl.² ........................................... B01D 3/34
[58] Field of Search ............... 203/9, 8; 260/669 A; 423/386

[56] References Cited
UNITED STATES PATENTS

| | | | |
|---|---|---|---|
| 3,527,822 | 9/1970 | Benson, Jr. ............... | 260/669 A |
| 3,816,265 | 6/1974 | Daniels et al. ............ | 203/9 |

*Primary Examiner*—Norman Yudkoff
*Assistant Examiner*—M. G. Mullen
*Attorney, Agent, or Firm*—Bacon & Thomas

[57] ABSTRACT

Disclosed is a process for the distillation of readily polymerizable vinyl aromatic compounds which comprises subjecting such compounds to distillation conditions in the presence of an effective amount of NOCl as a polymerization inhibitor in the substantial absence of oxygen.

8 Claims, No Drawings

NITROSYL CHLORIDE AS A POLYMERIZATION INHIBITOR FOR VINYL AROMATIC COMPOUNDS

BACKGROUND OF THE INVENTION

The present invention relates to a process for the distillation of readily polymerizable vinyl aromatic compounds, and more especially, to a process for the vacuum distillation of styrene, substituted styrene, divinylbenzene and polyvinylbenzenes wherein the amount of said materials polymerized during distillation is reduced over an extended period of time, wherein the material accummulating in the bottom or reboiler area of the distillation apparatus is free of material contaminated with sulfur and wherein the rate of throughput for a given distillation apparatus can be increased over the rate at which such apparatus may be operated in accordance with conventional methods.

It is well known that vinyl aromatic compounds such as monomeric styrene, lower alkylated styrene, e.g., alphamethyl styrene, and divinylbenzene polymerize readily, and furthermore, that the rate of polymerization increases with increasing temperature. Inasmuch as styrene and divinylbenzene produced by common industrial methods contain impurities, these compounds must be subjected to separation and purification processes in order to be suitable for most types of further industrial use. Such separation and purification is generally accomplished by distillation.

In order to prevent polymerization during distillation of vinyl aromatic compounds, various types of known polymerization inhibitors have been employed in connection with prior art distillation processes. For example, common inhibitors useful for inhibiting the polymerization of vinyl aromatics under distillation conditions include 4-tert-butylcatechol (TBC) and hydroquinone. It is preferred, however, to purify vinyl aromatics by using vacuum distillation techniques, whereby these commonly employed inhibitors are rendered unsuitable in view of the fact that they are effective only in the presence of oxygen. The partial pressure of oxygen in a vacuum distillation column is accordingly too low for these conventional inhibitors to be effective. Sulfur is perhaps the polymerization inhibitor most commonly employed to inhibit polymerization of vinyl aromatic compounds during distillation, since sulfur does provide effective inhibition in the absence of oxygen. While sulfur provides a reasonably effective inhibitor, its use in distillation processes results in one very significant disadvantage, namely, there is formed in the reboiler bottoms of the distillation column a valueless waste material which is highly contaminated with sulfur. This waste material furthermore represents a significant pollution or waste removal problem.

Although many compounds are effective for inhibiting the polymerization of vinyl aromatic compounds under differing conditions, e.g., storage, other purification techniques, etc., for a number of reasons which are not entirely understood in view of the diverse and unpredictable results obtained, only extremely few of these compounds have proved to be of any utility for inhibiting vinyl aromatic polymerization under distillation conditions, particularly under vacuum distillation conditions. In addition, certain compounds which are useful for inhibiting polymerization of one type of vinyl aromatic compound, for example, styrene, have proved to be essentially ineffective for inhibiting polymerization of another species of vinyl aromatic compound, for example, divinylbenzene. A limited number of nitroso compounds have proven to be effective for inhibiting polymerization of styrene monomer during distillation. For example, N-nitroso phenylhydroxylamine and p-nitroso-N,N-dimethylaniline are reasonably effective inhibitors for the distillation of styrene, although they are not particularly soluble in styrene monomer. On the other hand, N-nitroso diphenylamine disclosed in U.S. Pat. No. 3,816,265, assigned to the assignee of the present application has been demonstrated to be a particularly effective polymerization inhibitor under vacuum distillation conditions for both styrene and divinylbenzene, whereas N,N-nitrosomethylaniline as disclosed in U.S. patent application Ser. No. 288,138, also assigned to the assignee of the present application, has been found to be an excellent polymerization inhibitor for styrene under vacuum distillation conditions. One of the most effective inhibitor systems known for divinylbenzene comprises a mixture of sulfur and N-nitroso phenylhydroxylamine.

In a typical distillation process for vinyl aromatic compounds utilizing a polymerization inhibitor, the mixture of vinyl aromatic to be distilled is generally contacted with the chemical polymerization inhibitor prior to being subjected to distillation conditions in the distillation apparatus. It remains as a significant problem today that the amount of polymer formed in the distillation apparatus and in the high purity product recovered therefrom is substantially higher than desired, and occasionally, that complete polymerization occurs inside of the distillation apparatus. For example, in the process of distilling crude divinylbenzene (a mixture containing divinylbenzenes, diethylbenzenes and monovinylbenzenes) to obtain high purity divinylbenzenes, even when inhibited with sulfur and TBC, a divinylbenzene product is obtained which contains significant quantities of polymer which are difficult to separate from the product and are detrimental to the end use of such divinylbenzenes. Furthermore, the material which is removed from the bottom or reboiler area of the distillation apparatus is a highly polluting sulfur-containing waste material which must be disposed of.

Nitrogen oxides are known according to the prior art to be effective for inhibiting polymerization of certain unsaturated compounds, and accordingly, have been employed as polymerization inhibitors in certain types of applications. However, the use of the normally-gaseous nitrogen oxides is predominantly confined to static conditions, e.g., storage, since the use of a gaseous material is strongly suggested against under any conditions where the inhibitor could readily escape. Thus, the use of normally gaseous inhibitors such as the nitrogen oxides has found substantially no application in distillation or similar purification processes involving heat, and this is particularly true in the case of vacuum distillation for the obvious reasons.

Accordingly, there exists a strong need for a polymerization inhibitor which will effectively prevent the polymerization of vinyl aromatic compounds during vacuum distillation thereof.

SUMMARY OF THE INVENTION

It is therefore an object of the present invention to provide a new and improved process for the distillazation of readily polymerizable vinyl aromatic compounds.

A further object of the invention is to provide a new and improved process for the distillation of readily polymerizable vinyl aromatic compounds, which process results in higher recovery of a high purity unsaturated vinyl aromatic compound and concomitantly in the production of less undesirable by-products.

A further object of the invention resides in the provision of a new and improved process for the distillation of vinyl aromatic compounds which results in the production of substantially less polymerized material in the distillation apparatus.

Yet another object of the invention resides in the provision of a new and improved process for the distillation of vinyl aromatic compounds which avoids the production of a highly polluting, contaminated bottom or reboiler residue.

It is also an object of the present invention to provide a new and improved process for the distillation of vinyl aromatic compounds which permits the distillation apparatus to be operated at an increased rate of throughput without a reduction in efficiency.

It is still a further object of the present invention to provide a new and improved process for the distillation of vinyl aromatic compounds which provides all of the foregoing-enumerated advantages in a vacuum distillation process.

In accomplishing the foregoing and other objects, there has been provided in accordance with the present invention a process for the distillation of a readily polymerizable vinyl aromatic compound comprising subjecting the vinyl aromatic compound to distillation conditions in the presence of an amount of NOCl and in the substantial absence of oxygen to inhibit polymerization of the vinyl aromatic compound under the distillation conditions.

In one aspect of the process according to the invention, the normally gaseous inhibitor is simply introduced into the distillation system by injection into the reboiler area of the distillation apparatus, or alternatively, by injection into the incoming stream of vinyl aromatic compound to be purified. It is one salient feature of the invention that the mode of introducing and metering the amount of polymerization inhibitor is considerably simplified due to the ease of metering a normally gaseous material and due to the simplicity of the equipment necessary therefor.

The amount of NOCl necessary to inhibit polymerization of the vinyl aromatic compounds may vary over a broad range depending upon various factors of the distillation process e.g., temperature, amount of reflux, if any, pressure, residence time, etc. Typically, however, it has been found that an amount of inhibitor between about 100 and about 1,000 ppm is sufficient to substantially inhibit polymerization of vinyl aromatic compounds under normal distillation conditions. (105°C.)

Through the use of the process according to the present invention, the amount of polymerization occurring within the distillation apparatus is significantly reduced in comparison to conventionally employed methods. In addition, the amount of desired distillation product is increased in proportion to the decrease in the amount of polymer formation. Also, the rate of operation of a given distillation apparatus can be increased over and above the rate of operation for the same apparatus utilizing conventional methods, since lower vacuum levels and higher distillation temperatures are possible according to the present invention. Still further, the material accummulating in the bottom or reboiler area of the distillation apparatus can be reused, e.g., for its fuel value or for reprocessing, which is a distinct advantage over conventional methods utilizing sulfur as a polymerization inhibitor which produce a highly polluting waste material in the reboiler area. Furthermore, it has also been found that any polymeric material inadvertently formed during the process of the invention is of a low molecular weight character and therefore presents fewer problems in connection with fouling of the distillation apparatus. Finally, use of the inhibitor according to the invention has proven to be surprisingly advantageous in preventing polymer build-up over the entire extent of the distillation apparatus, i.e., in the upper portions of the columns, whereas this result is not achieved in accordance with prior art methods.

DETAILED DESCRIPTION OF PREFERRED EMBODIMENTS

The distillation process of the present invention employs nitrosyl chloride (NOCl) as a polymerization inhibitor during the distillation process carried out under reduced pressure, e.g., vacuum distillation, and one of the significant advantages of the invention is that the use of sulfur in the distillation system can be avoided.

The distillation technique of the process of the present invention is suitable for use in virtually any type of separation of a readily polymerizable vinyl aromatic compound from a mixture wherein the vinyl aromatic compound is subjected to temperatures above room temperature. Surprisingly, the process of the present invention has been found particularly useful in vacuum distillation techniques, the preferred method for separating unstable organic liquid mixtures. In its most useful application, the distillation process of the invention is applied to a distillation mixture containing one of the vinyl aromatic compounds selected from the group consisting of styrene, alpha-methylstyrene, vinyltoluene, vinylnaphthalene, divinylbenzenes and polyvinylbenzenes. The preferred application of the present invention relates to the distillation of crude divinylbenzene or crude styrene under vacuum distillation conditions.

The amount of polymerization inhibitor added may vary over a wide range depending upon the conditions of distillation. Generally, the degree of stabilization is proportional to the amount of inhibitor added. In accordance with the present invention, it has been found that inhibitor concentrations generally between about 100 and about 1,000 ppm have generally provided suitable results, depending primarily upon the temperature of the distillation mixture and the degree of inhibition desired.

During vacuum distillation of divinylbenzene-containing mixtures and styrene-containing mixtures, the temperature of the reboiler is preferably maintained from about 150°F. to about 250°F. by controlling reboiler pressure at from about 30 mm. to about 400 mm. of Hg. Under such conditions, in a distillation apparatus having a distillation zone containing from about 50 to about 100 distillation stages, inhibitor concentrations of from about 100 to about 3,000 ppm are suitable, whereas concentrations of from about 100 to about 1,000 ppm are preferred in the case of styrene distillation and concentrations in the range of from about 100 to about 2,000 ppm are preferred for distillation of vinylbenzenes. Obviously, amounts of inhibitor greater than those specified hereinabove may be employed, although the advantages of adding the additional inhibitor are not significant and are outweighed by the corresponding increase in cost.

In addition, within the foregoing general ranges specified for the inhibitor concentration, preferred ranges have been developed. NOCl constitutes an excellent inhibitor over the entire temperature range likely to be encountered in distillation techniques. Because of its very effective nature as an inhibitor for vinyl aromatic compounds, NOCl is preferably employed in an amount of from about 100 to 500 ppm in the distillation of styrene compounds and in an amount of from about 100 to 1,000 ppm in the distillation of divinylbenzene at temperatures between about 150° and 300°F., preferably between 200° and 300°F., for styrene and residence times between about 2 and 4 hours. Obviously, in the lower portions of the temperature and residence time ranges, smaller amounts of inhibitor are required.

The normally gaseous polymerization inhibitor of the present invention may be introduced into the distillation apparatus in any convenient manner which permits efficient distribution of the inhibitor throughout the apparatus. Typically and most advantageously, the required amount of gaseous inhibitor is simply injected into the reboiler area of the distillation column, although equivalent results may be obtained by injecting the inhibitor into the incoming hot stream of vinyl aromatic compound. The gaseous nature of the inhibitor according to the invention provides significant advantages in terms of the ease with which addition of the inhibitor may be accomplished. Thus, the apparatus necessary for including the inhibitor may be greatly simplified over that required to introduce conventional inhibitors, since simple injection valves and conventional metering systems may be readily adapted for this purpose. In this way, control of the amount of inhibitor added is particularly simplified.

Since the inhibitor is gradually depleted during operation, it is generally necessary to maintain the appropriate amount of inhibitor in the distillation apparatus by adding inhibitor during the course of the distillation process. Such addition may be carried out either on a generally continuous basis or it may consist of intermittent charging of inhibitor into the distillation system. A means by which the maintenance of the necessary inhibitor concentration is carried out is of no particular importance as long as the concentration of inhibitor is kept above the minimum required level.

It has been found in accordance with the invention that the volitility of the inhibitor provides unexpected advantages in terms of the degree of inhibition of polymer achieved during the subject distillation process. The volitility of the inhibitor of the invention causes it to be more effectively distributed throughout the entire length of the distillation apparatus. As a result, polymerization is more effectively inhibited at points in the apparatus remote from the reboiler area than is the case with conventional distillation processes using liquid or solid inhibitors. The need for adding inhibitor at various points in the distillation column is therefore eliminated.

Another factor enabling the distillation apparatus to operate at an increased rate in accordance with the present invention as opposed to conventional prior art processes is the fact that the inhibitor of the present invention is a more efficient inhibitor than the conventional inhibitors, and will thus permit higher distillation temperatures and higher pressures. In this way, the rate of distillation can be increased without increasing the amount of polymerization which has been deemed to be acceptable in accordance with conventional distillation procedures.

When the process of the present invention is utilized, the bottoms material which accummulates during the distillation process can be drawn off and utilized for its heating value or for reprocessing. This represents another significant advantage in comparison to conventional processes for vacuum distillation of vinyl aromatic compounds which employ sulfur as the polymerization inhibitor, or sulfur in combination with other chemical polymerization inhibitors. In these conventional processes, a bottoms material is formed which is valueless for further use and constitutes a highly polluting waste material which must be disposed of and which, in this regard, also presents a problem of disposal. Detonability studies have been conducted on the bottoms material produced in accordance with the present invention, and it has been found that these materials do not possess any dangerous characteristics. This too represents an unexpected finding in accordance with the invention, since it was strongly suspected that the bottoms material might contain residual nitro groups as a result of using NO as a polymerization inhibitor.

Upon recovery of the distillation product obtained from the process of the present invention, it is found that a higher percentage of the pure readily polymerizable vinyl aromatic compound is recovered in an unpolymerized state. Furthermore, it has been noted that the polymeric products which are formed during the distillation process of the invention exhibit significantly lower molecular weight characteristics than polymeric products formed in accordance with conventional distillation techniques in the presence of the usual inhibitors. This result provides the advantage that there is less fouling in the apparatus and accordingly less chance of plugging. Moreover, the concentrated distillation residues are more easily handled and removed from the apparatus, as by pumping or the like.

Nitrosyl chloride (NOCl) is a normally gaseous compound at room temperature and above. Because of its boiling point of −5°C., however, it is suitably adapted for liquification under increased pressure conditions for storage and transportation at normal temperatures. This compound is readily available commercially.

In order to more fully explain the present invention, the following Examples are presented which are intended to be merely illustrative and not in any sense limitative of the invention.

EXAMPLE 1

50 ml. of styrene containing 1,000 ppm of N-nitroso diphenylamine are charged to a control flask, and 50 ml. of styrene are charged to a sample flask. Both flasks are flushed with nitrogen to remove all dissolved oxygen, then a continuous nitrogen sweep is afixed to the control flask. 8.1 ml (0.02g.) of NOCl is injected into the contents of the control flask. Both flasks are placed in an oil bath heated to 115°C. and agitation is provided in each. Samples are periodically taken and tested by combining 1 ml. samples with 3 ml. of methanol and examining for turbidity. The following results are obtained:

After 1 hour the control flask evidences the formation of styrene polymer in accordance with the test, whereas the sample flask shows no formation of polymer. Samples are taken from the sample flask at half hour intervals and checked for polymer formation. After 3½ hours still no turbidity is detectable. After 4 hours turbidity is barely noticable in the tested portion; and after 4½ hours the tested portion is noticably turbid. The results show that a single addition of NOCl is sufficient to inhibit styrene polymerization under distillation conditions over a 4½ hour period. The amount of NOCl utilized corresponds to about 400 ppm. based upon the styrene.

EXAMPLE 2

The procedure set forth in Example 1 is repeated, except that 4 ml (about 200 ppm.) NOCl is added to the initial charge of 50 grams of styrene in the heated bath. Samples are taken at half-hour intervals to investigate for the presence of polymer. No polymer is detected during the first 2 hours of the test; however, very slight turbidity is noticed at 2½ hours, and significant turbidity is noticed after 3 hours, although no precipitation of polymer occurs. The results show that 200 ppm of NOCl provides a very good degree of inhibition.

EXAMPLE 3

The procedure of Example 2 is repeated utilizing 400 ppm. NOCl, but with immersion of the flask in an oil bath having a temperature of 130°C. The samples of styrene are taken each half hour for testing. Protection is afforded for a period of about 2 hours, after which the test samples show turbidity, but do not coagulate.

EXAMPLE 4

30 ml. of divinylbenzene (containing 81 percent meta-isomer, 11.2 percent para-isomer, 7.6 percent naphthenes and 0.2 percent meta-ethylvinyl-benzene) is withdrawn from storage and sealed in a 50 ml. flask with a septum closure. The divinylbenzene exhibits a faint cloud on testing with methanol, which indicates that some polymer has been formed upon storage. The flask is purged with nitrogen to remove all oxygen, and then 400 ppm of NOCl gas is injected into the flask. The flask is placed in an agitated temperature controlled oil bath at 105°C., and no additional cloud is observed as a result of the methanol test conducted after 1 hour at this temperature. The temperature of the bath is increased to 110°C. and is maintained there for 1 hour. A sample taken for the methanol test again shows no increase in turbidity. The temperature of the bath is increased to 115°C., and a sample is taken and tested after about 40 minutes. This sample shows a definite increase in turbidity but the sample is not opaque and does not coagulate, which indicates that the polymer content is still below the 1 percent level.

EXAMPLE 5

The procedure of Example 4 is repeated except that 250 ppm of N-nitroso diphenylamine is employed in place of the NO. After 3/4 of an hour at 105°C. it is observed that the flask is approximately half filled with insoluble polymer. Upon removal of the flask from the bath, polymerization still continues and explodes the flask in approximately 1 minute, leaving dry solid pieces of insoluble polymer. Essentially 100 percent polymerization is observed.

What is claimed is:

1. A process for the distillation of a readily polymerizable vinyl aromatic compound, which comprises subjecting such compound to distillation conditions in the presence of nitrosyl chloride (NOCl) as a polymerization inhibitor and in the substantial absence of oxygen.

2. The process as defined by claim 1, wherein said distillation conditions are vacuum distillation conditions.

3. The process as defined by claim 1, wherein said nitrosyl chloride polymerization inhibitor is continuously added to said vinyl aromatic compound.

4. The process as defined by claim 1, wherein said vinyl aromatic compound is styrene.

5. The process as defined by claim 1, wherein said vinyl aromatic compound is divinylbenzene.

6. The process as defined by claim 1, wherein said inhibitor is present in an amount of from about 100 ppm to about 3,000 ppm.

7. The process as defined by claim 1, wherein said distillation conditions comprise a temperature between about 150° and 300°F.

8. The process as defined by claim 7, wherein said temperature is between about 200° and 300°F.

* * * * *